US00PP30423P2

(12) United States Plant Patent
Carney et al.

(10) Patent No.: US PP30,423 P2
(45) Date of Patent: Apr. 23, 2019

(54) CHERRY TREE NAMED 'CARNEVAL'

(50) Latin Name: *Prunus avium*
Varietal Denomination: Carneval

(71) Applicant: Kevin Scott Carney, Cashmere, WA (US)

(72) Inventors: Kevin Scott Carney, Cashmere, WA (US); Neil Johnson, Cashmere, WA (US)

(73) Assignee: Kevin Scott Carney, Cashmere, WA (US)

( * ) Notice: Subject to any disclaimer, the term of this patent is extended or adjusted under 35 U.S.C. 154(b) by 0 days.

(21) Appl. No.: 15/732,240

(22) Filed: Oct. 10, 2017

(51) Int. Cl.
*A01H 5/08* (2018.01)

(52) U.S. Cl.
USPC ..... Plt./181
CPC ..... *A01H 5/08* (2013.01)

(58) Field of Classification Search
USPC ..... Plt./181
CPC ..... A01H 5/085
See application file for complete search history.

*Primary Examiner* — Kent L Bell
(74) *Attorney, Agent, or Firm* — Michelle Bos Legal LLC

(57) ABSTRACT

The 'Carneval' sweet cherry tree is distinguished by its very early bloom, early harvest maturity, and large, high quality fruit.

6 Drawing Sheets

Latin name: *Prunus avium.*
Variety denomination: 'Carneval'.

BACKGROUND OF THE VARIETY

'Carneval' is a new and distinct variety of sweet cherry tree that originated as a whole tree mutation of unknown origin. 'Carneval' was discovered in the inventor's 'Skeena' (U.S. Plant Pat. No. 11,392) cherry orchard in Cashmere, Wash. in 2008, and was originally selected for further observation because of its early bloom and early harvest maturity. 'Carneval' was first asexually propagated by budding in 2015 at Cashmere, Wash., and has since been observed to remain true to type over successive asexually propagated generations.

BRIEF DESCRIPTION OF THE VARIETY

The 'Carneval' sweet cherry tree is distinguished by its very early bloom, early harvest maturity, and large, high quality fruit.

'Carneval' is distinguished from similar varieties 'PC 7146-23' (U.S. Plant Pat. No. 8,545) and 'Skeena' (U.S. Plant Pat. No. 11,392) by its early bloom, which occurs 7 to 14 days earlier than 'Skeena' and 2 days earlier than 'PC 7146-23'. 'Carneval' cherries are ready for harvest about 15 days before 'Skeena' and about 2 days before 'PC 7146-23'. Mature 'Carneval' cherries are similar in size to 'Skeena' cherries and larger than 'PC 7146-23' cherries.

BRIEF DESCRIPTION OF THE PHOTOGRAPHS

Figure 1:
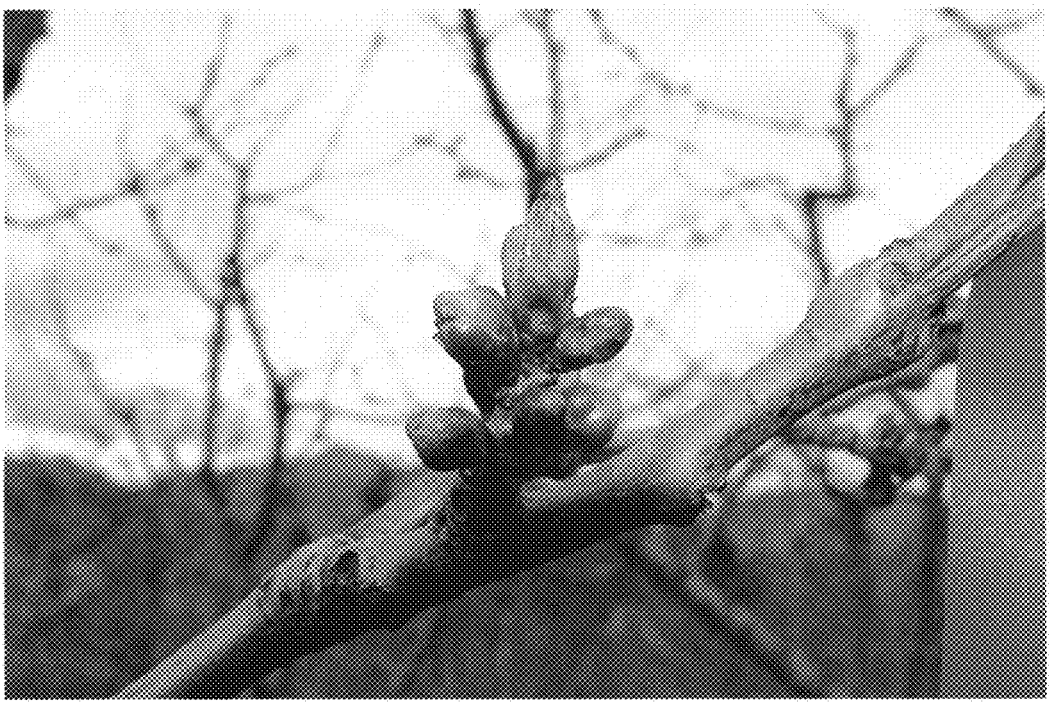
FIG. 1 shows buds on a 'Carneval' cherry tree in early April.
Figure 2:
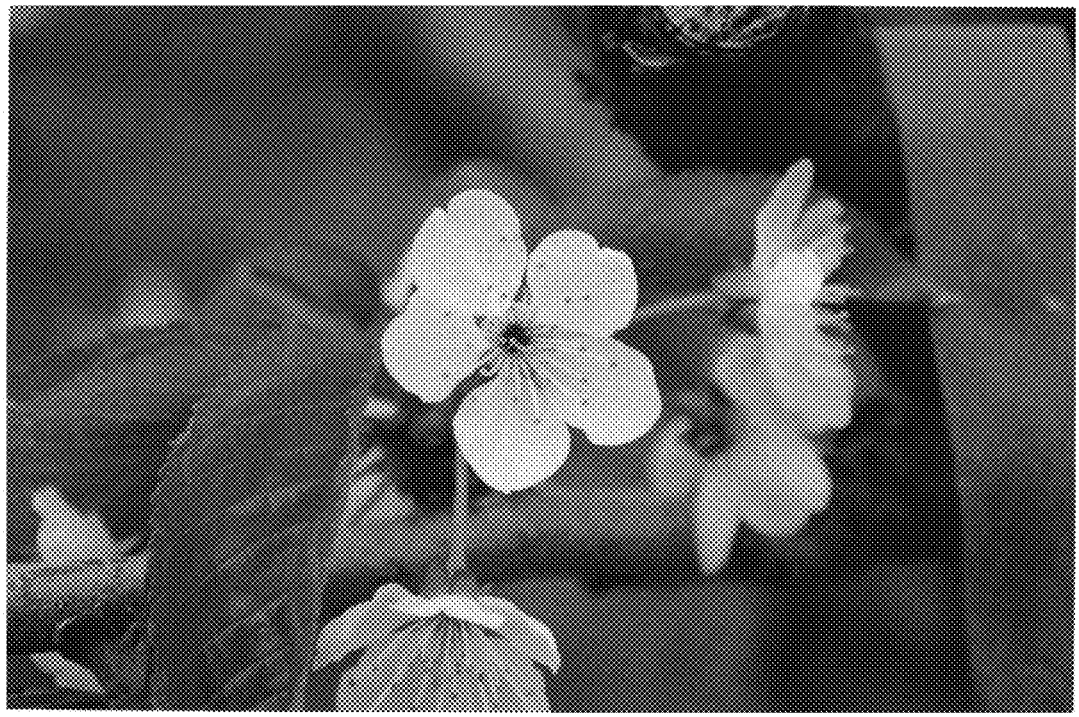
FIG. 2 shows blooms on a 'Carneval' tree in late April.
Figure 3:
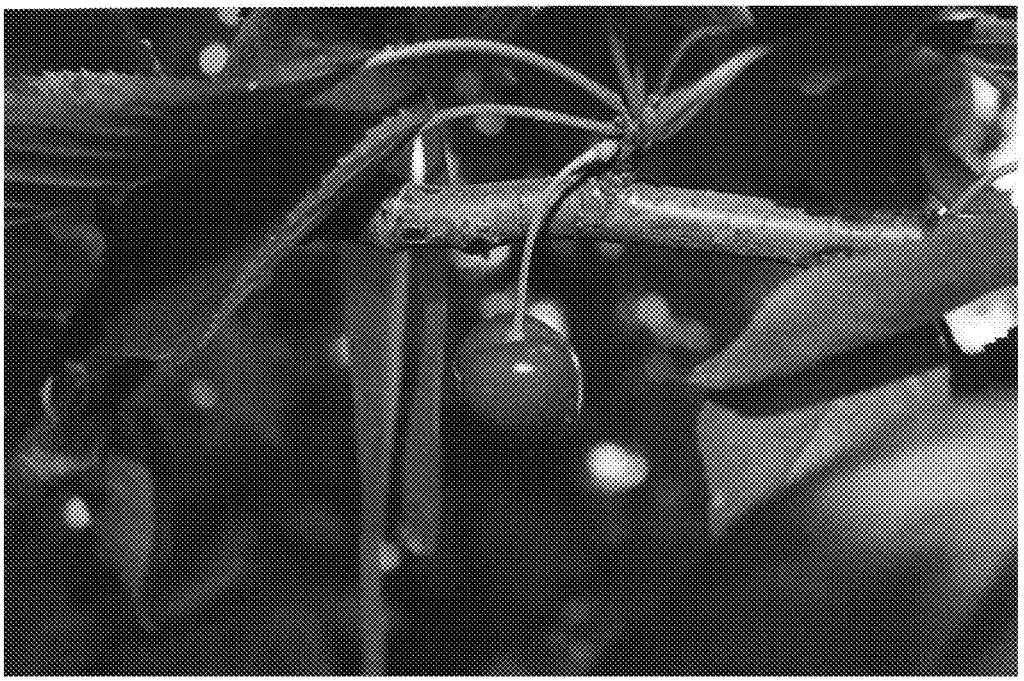
FIGS. 3 and 4 show cherries on a 'Carneval' tree in late June.
Figure 4:
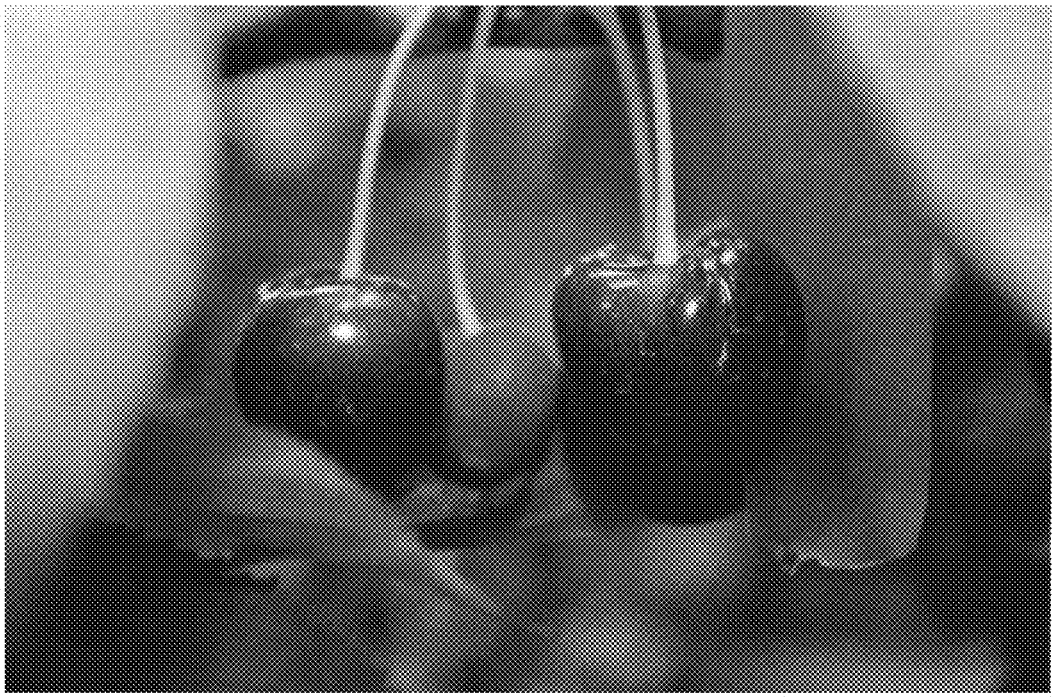
Figure 5:
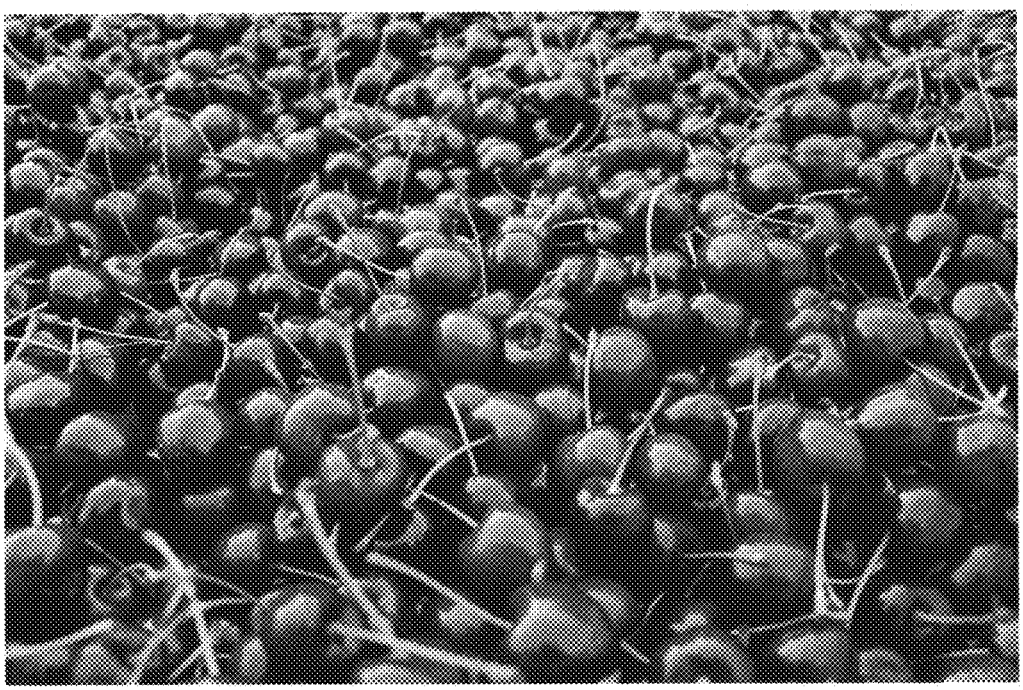
FIG. 5 shows freshly picked 'Carneval' cherries.
Figure 6:
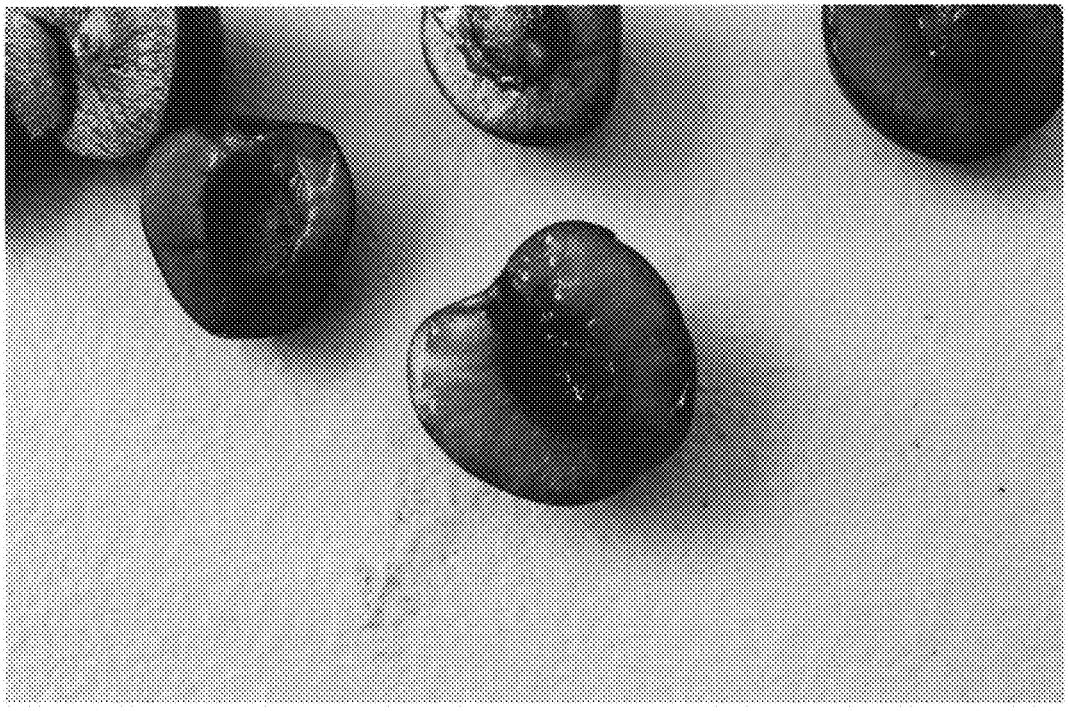
FIG. 6 shows sectioned 'Carneval' cherries.

Actual colors will vary with lighting conditions; color characteristics of 'Carneval' cherry tree should therefore be determined with reference to the observations described herein below, rather than from these illustrations alone.

DETAILED BOTANICAL DESCRIPTION OF THE VARIETY

The attached illustrations and the following detailed botanical description of 'Carneval' sweet cherry tree are based on observations made and photos taken during the 2017 growing season near Cashmere, Wash., of trees planted in 2004 on 'Mazzard' rootstock. All colors are described according to The Royal Horticultural Society Colour Chart ($6^{th}$ edition). The characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Typical of sweet cherry varieties.
*Habit, shape.*—Ramified; columnar if unmanaged.
*Height.*—4.2 m.
*Trunk diameter* (*at* 30 *cm above the graft*).—32.2 cm.
*Bark texture.*—Rough.
*Bark color.*—Grey N201B.

Branch (fruiting branches located at around 1 m above the graft union):

*Length.*—23.2 cm.
*Diameter.*—5.1 cm.
*Crotch angle.*—27°.
*Color.*—Grey N201B.
*Texture.*—Slightly rough with raised lenticels.
*Lenticel length.*—0.7 to 1.0 mm.
*Lenticel color.*—White N155B.
*Lenticel quantity.*—Few, 1 to 2 per $cm^2$.

One year old shoot:
*Length.*—19.5 cm.
*Diameter.*—6.1 mm.
*Color.*—Grey-Brown N199D.
*Pubescence.*—None.
*Internode length.*—9.3 cm.
*Lenticel length.*—0.75 mm to 1.20 mm.
*Lenticel color.*—White N155C.
*Lenticel quantity.*—Few, 1-2 per $cm^2$.

Flower buds:
*Quantity per spur.*—3 to 5.
*Shape.*—Conical.
*Length.*—8.5 mm.
*Diameter.*—4.6 mm.
*Color.*—Greyed-orange 166C.

Flowers:
*Diameter of fully open flower.*—37 mm.
*Relative position of petal margin.*—Touching.
*Flower depth.*—4.5 mm to 4.8 mm.
*Pedicel length.*—21 mm.
*Pedicel diameter.*—1.5 mm.
*Pedicel color.*—Strong yellow-green 144B.
*Number of flowers per cluster.*—3 to 5.
*Date of first bloom.*—April 19.
*Date of full bloom.*—April 22.
*Pollination requirement.*—Unknown; possibly self-fertile.

Petals:
*Number per flower.*—5.
*Length.*—13 mm.
*Width.*—14 mm.
*Petal shape.*—Orbicular.
*Apex shape.*—Retuse.
*Base shape.*—Rounded.
*Margin.*—Smooth.
*Color of upper surface.*—White NN155D.
*Color of lower surface.*—White NN155D.

Pistil:
*Length.*—6 to 14 mm.
*Color.*—White NN155D.

Stigma:
*Diameter.*—1 mm.
*Color.*—Strong greenish-yellow 151B.

Style:
*Length.*—12 mm.
*Color.*—Brilliant yellow-green 150C.

Ovary:
*Size.*—Length 3 mm, width 2 mm.
*Color.*—Strong yellow-green N144C.

Stamens:
*Quantity.*—About 31 per flower.
*Anther size.*—Length 0.75 mm.
*Anther color.*—Vivid yellow 15A.
*Pollen.*—Present, vivid yellow 15A.

Sepals:
*Quantity.*—5.
*Color.*—Strong yellow green 144B.
*Shape.*—Oblong.
*Apex.*—Rounded.
*Margin.*—Smooth.

Leaves:
*Length.*—14.8 cm.
*Width.*—6.6 cm.
*Blade margin.*—Bi-serrate.
*Leaf shape.*—Elliptic.
*Leaf texture.*—Upper surface — Smooth.
*Leaf texture.*—Lower surface — Smooth with prominent veins.
*Apex shape.*—Acuminate.
*Base shape.*—Rounded.
*Attitude in relation to shoot.*—Outward to upward.
*Color of upper surface.*—Yellow-green 147A.
*Color of lower surface.*—Yellow-green 148A.

Petiole:
*Length.*—38.5 mm.
*Diameter.*—2.5 mm.
*Color.*—Yellow-green 144D.

Fruit:
*Quantity per cluster.*—3 to 4.
*Diameter.*—27 mm.
*Length.*—28 mm.
*Weight.*—11.3 g.
*General shape in profile.*—Cordate to reniform.
*Shape of stem end.*—Slightly depressed.
*Shape of apex.*—Flat.
*Diameter of stalk cavity.*—7 cm.
*Depth of stalk cavity.*—5 mm.
*Suture.*—Absent or weakly conspicuous.

Skin:
*Texture.*—Smooth.
*Ground color.*—Light purplish pink 62C.
*Over color.*—Intense dark red 59A solid flush overcolor on 90% of fruit surface.
*Taste.*—Sweet, more acidic than 'PC 7146-23'.

Stalk:
*Length.*—45 mm.
*Diameter.*—2 mm.
*Color.*—Strong yellow-green 144C.

Flesh:
*Firmness of flesh.*—Firm, 371 FirmTech firmness rating.
*Flesh texture.*—Fine.
*Fibers.*—Not fibrous.
*Aroma.*—Typical of sweet cherry.
*Juiciness.*—Similar to 'Bing'.
*Brix.*—21.3° Brix.
*Flesh color.*—Strong red 53B.

Stone:
*Length.*—11 mm.
*Diameter.*—9 mm.
*Shape.*—Oblong.
*Texture.*—Smooth.
*Tendency to split.*—Rare.
*Color.*—Pale yellow 154D.

Kernel:
*Length.*—8.0 to 8.2 mm.
*Width.*—5.0 mm.
*Depth.*—2.7 to 3.0 mm.
*Shape.*—Oblong.
*Texture.*—Wrinkled.
*Color.*—Brownish orange N167A.

Harvest:
*Time for harvest.*—Early; complete harvest Jun. 23, 2017.
*Number of picks.*—1.
*Productivity.*—Average 71 pounds per tree in 2017.

*Cold hardiness*.—Hardy in area tested.

*Disease resistance/susceptibility*.—None noted.

*Market use*.—Fresh.

*Keeping quality*.—Typical of sweet cherry.

I claim:

1. A new and distinct cherry tree, substantially as described and illustrated herein.

* * * * *